United States Patent
Lorsch

(10) Patent No.: US 8,725,537 B2
(45) Date of Patent: May 13, 2014

(54) METHOD AND SYSTEM FOR PROVIDING ONLINE RECORDS

(75) Inventor: Robert H. Lorsch, Los Angeles, CA (US)

(73) Assignee: MyMedicalRecords, Inc., Los Angeles, CA (US)

( * ) Notice: Subject to any disclaimer, the term of this patent is extended or adjusted under 35 U.S.C. 154(b) by 1410 days.

(21) Appl. No.: 12/204,498

(22) Filed: Sep. 4, 2008

(65) Prior Publication Data

US 2009/0055894 A1 Feb. 26, 2009

Related U.S. Application Data

(63) Continuation-in-part of application No. 11/225,518, filed on Sep. 12, 2005, now Pat. No. 8,121,855.

(51) Int. Cl.
- *G06Q 50/18* (2012.01)
- *A61B 5/00* (2006.01)
- *G06F 19/00* (2011.01)
- *G06Q 50/00* (2012.01)

(52) U.S. Cl.
USPC .................................................. 705/3; 705/2

(58) Field of Classification Search
USPC ........................................................ 705/2–3
See application file for complete search history.

(56) References Cited

U.S. PATENT DOCUMENTS

| | | | |
|---|---|---|---|
| 5,404,292 A | 4/1995 | Hendrickson | |
| 5,494,292 A | 2/1996 | Mileti | |
| 5,499,293 A | 3/1996 | Behram et al. | |
| 5,778,882 A | 7/1998 | Raymond et al. | |
| 5,832,488 A | 11/1998 | Eberhardt | |

(Continued)

FOREIGN PATENT DOCUMENTS

| | | |
|---|---|---|
| EP | 0 764 911 A1 | 3/1997 |
| JP | 9-218902 | 8/1997 |
| JP | 2001-350847 | 12/2001 |

OTHER PUBLICATIONS www.biscom.com, Biscom website, Mar. 2005, faxcom_healthcare.htm, fax_facts.htm, mercyhealth.htm, ge.htm, stfrancis.html, faxcom_web_client.htm, bpm.htm.*

(Continued)

*Primary Examiner* — Joy Chng
(74) *Attorney, Agent, or Firm* — McKee, Voorhees & Sease

(57) ABSTRACT

A method for providing a user with the ability to access and collect legal records associated with the user includes assigning a phone number to the user for fax and voice communications from a legal services provider, associating access information with the user for the user to use to access a secure web site, providing the user with a document to provide to the legal services provider exercising rights of the user for access to the legal records, the document requesting the legal services provider to send the legal records to the phone number, receiving a private fax communication comprising a legal record associated with the consumer for which the consumer has requested and given permission to the legal services provider to send, converting the private fax communications into an image file format, storing the legal services record encoded in the image file format, and providing the user with secure access to the web site using the access information and providing on the web site an interface to the legal records of the user for the user to access the legal record.

28 Claims, 11 Drawing Sheets

(56) References Cited

U.S. PATENT DOCUMENTS

| | | |
|---|---|---|
| 5,924,074 A | 7/1999 | Evans |
| 5,926,526 A | 7/1999 | Rapaport et al. |
| 5,930,759 A * | 7/1999 | Moore et al. ............... 705/2 |
| 5,970,463 A | 10/1999 | Cave et al. |
| 5,974,124 A | 10/1999 | Schlueter, Jr. et al. |
| 5,997,476 A | 12/1999 | Brown |
| 6,000,828 A | 12/1999 | Leet |
| 6,032,119 A | 2/2000 | Brown et al. |
| 6,073,106 A | 6/2000 | Rozen et al. |
| 6,082,776 A * | 7/2000 | Feinberg ............... 283/72 |
| 6,088,677 A | 7/2000 | Spurgeon |
| 6,223,559 B1 | 5/2001 | Coleman |
| 6,463,417 B1 | 10/2002 | Schoenberg |
| 6,523,009 B1 | 2/2003 | Wilkins |
| 6,574,484 B1 | 6/2003 | Carley |
| 6,651,060 B1 | 11/2003 | Harper et al. |
| 6,654,724 B1 | 11/2003 | Rubin et al. |
| 6,725,200 B1 | 4/2004 | Rost |
| 6,738,784 B1 | 5/2004 | Howes |
| 6,845,448 B1 | 1/2005 | Chaganti et al. |
| 6,871,214 B2 * | 3/2005 | Parsons et al. ............... 709/206 |
| 6,941,271 B1 | 9/2005 | Soong |
| 6,954,802 B2 | 10/2005 | Sutherland et al. |
| 6,988,075 B1 * | 1/2006 | Hacker ............... 705/3 |
| 7,257,967 B2 | 8/2007 | Rheinstein |
| 7,287,031 B1 | 10/2007 | Karpf et al. |
| 7,306,560 B2 | 12/2007 | Iliff |
| 7,428,494 B2 | 9/2008 | Hasan et al. |
| 7,440,904 B2 | 10/2008 | Hasan et al. |
| 7,475,020 B2 | 1/2009 | Hasan et al. |
| 7,509,264 B2 | 3/2009 | Hasan et al. |
| 7,533,030 B2 | 5/2009 | Hasan et al. |
| 7,661,146 B2 | 2/2010 | Karimzadeh et al. |
| 7,685,003 B2 | 3/2010 | Hasan et al. |
| 7,693,730 B2 | 4/2010 | Hasan et al. |
| 7,707,047 B2 | 4/2010 | Hasan et al. |
| 7,720,691 B2 | 5/2010 | Hasan et al. |
| 7,827,043 B2 | 11/2010 | Tahan |
| 7,865,373 B2 | 1/2011 | Punzak et al. |
| 7,996,244 B1 | 8/2011 | Fitch |
| 8,010,717 B2 | 8/2011 | Evans et al. |
| 8,024,273 B2 | 9/2011 | Deobhakta et al. |
| 8,041,749 B2 | 10/2011 | Beck |
| 8,073,710 B2 | 12/2011 | Hasan et al. |
| 8,090,590 B2 | 1/2012 | Fotsch et al. |
| 8,108,311 B2 | 1/2012 | Herlitz |
| 8,131,563 B2 | 3/2012 | Hasan et al. |
| 8,135,596 B2 | 3/2012 | Jung et al. |
| 8,165,896 B2 | 4/2012 | Jung et al. |
| 8,180,654 B2 | 5/2012 | Berkman et al. |
| 8,214,234 B2 | 7/2012 | Hasan et al. |
| 8,301,466 B2 | 10/2012 | Lorsch |
| 2001/0041991 A1 * | 11/2001 | Segal et al. ............... 705/3 |
| 2002/0026332 A1 | 2/2002 | Snowden et al. |
| 2002/0046061 A1 | 4/2002 | Wright et al. |
| 2002/0059587 A1 | 5/2002 | Cofano et al. |
| 2002/0077861 A1 | 6/2002 | Hogan |
| 2002/0103675 A1 | 8/2002 | Vanelli |
| 2002/0111946 A1 * | 8/2002 | Fallon ............... 707/9 |
| 2002/0120470 A1 | 8/2002 | Trice, Sr. |
| 2002/0128865 A1 | 9/2002 | Alten |
| 2002/0138306 A1 | 9/2002 | Sabovich |
| 2002/0178631 A1 | 12/2002 | Morton |
| 2002/0189146 A1 | 12/2002 | Lyon |
| 2003/0014282 A1 | 1/2003 | Haaksma et al. |
| 2003/0037065 A1 | 2/2003 | Svab |
| 2003/0040940 A1 | 2/2003 | Nehammer |
| 2003/0059751 A1 | 3/2003 | Welles |
| 2003/0086591 A1 | 5/2003 | Simon |
| 2003/0098356 A1 | 5/2003 | Gombar |
| 2003/0132132 A1 | 7/2003 | Small |
| 2003/0140044 A1 * | 7/2003 | Mok et al. ............... 707/10 |
| 2003/0154411 A1 | 8/2003 | Hovik |
| 2003/0208382 A1 | 11/2003 | Westfall |
| 2003/0226889 A1 | 12/2003 | Morrison, Jr. |
| 2003/0229452 A1 | 12/2003 | Lewis et al. |
| 2003/0233384 A1 | 12/2003 | Nishii |
| 2004/0078229 A1 | 4/2004 | Gay et al. |
| 2004/0162895 A1 * | 8/2004 | Mok et al. ............... 709/223 |
| 2004/0186746 A1 | 9/2004 | Angst et al. |
| 2004/0199765 A1 | 10/2004 | Kohane et al. |
| 2004/0228336 A1 * | 11/2004 | Kung et al. ............... 370/352 |
| 2004/0267572 A1 | 12/2004 | Emery et al. |
| 2005/0165285 A1 | 7/2005 | Iliff |
| 2005/0209891 A1 | 9/2005 | Jacobus et al. |
| 2005/0251423 A1 | 11/2005 | Bellam et al. |
| 2006/0004588 A1 | 1/2006 | Ananda |
| 2007/0061169 A1 | 3/2007 | Lorsch |
| 2007/0061170 A1 | 3/2007 | Lorsch |
| 2008/0177669 A1 * | 7/2008 | Marshall ............... 705/80 |
| 2009/0007237 A1 | 1/2009 | Lorsch |

OTHER PUBLICATIONS www.linxcom.com, Jan. 7, 2005, Obtained from Internet Archive Wayback Machine (www.archive.org), linxconnect.htm, linxconnect_faq.htm.

http://web.archive.org/web/20050909014053/http://www.mbox.com.au, "mBox—Unified Messaging", printed off of Internet Aug. 11, 2009, 1 page.

Mymedicalrecords.com, Inc., PCT/US06/04867, Notification of Transmittal of International Preliminary Examination Report dated May 17, 2010.

MyMedicalRecords.com, Inc., Examiner's Report from Australian Patent Application No. 2006202057, dated Jul. 31, 2007, 2 pages.

Philip Marshall MD, MPH, WebMD Corporation, "Personal Health Records—An Overview", NCVHS Hearing, Jan. 6, 2005, 26 pages.

Internet Archive of 2005, http://www.personalmd.com [retrieved from the Internet on Apr. 24, 2013], 11 pages.

HealthData Management, "Is the Industry Ready to Get Personal", http://www.healthdatamanagement.com/issues/20_4/phr-personal-health-records-consumer . . . [retrieved from the Internet on Jan. 29, 2013], 8 pages.

Cohen, Perry, "Managed Care Pharmacy: Leading Pharmaceutical Care Integration Forward", Journal of Managed Care Pharmacy, vol. 3, No. 2, Mar./Apr. 1997, pp. 139-154.

Rite Aid News, http://www.riteaid.com/company/news/news_details.jsf?itemNumber=318 [retrieved from Internet on Apr. 2, 2012]. 2 pages.

Petition for Inter Partes Review of U.S. Patent No. 8,301,466 filed Feb. 13, 2013; Exhibits 1001-1025.

Heart Record Registration, https://web.archive.org/web/20010424161606/http://www.heartcenteronline.com/myheartdr/patientrecord/register.cfm, [retrieved from the internet on Nov. 7, 2013], 2 pages.

For Physicians, https://web.archive.org/web/20050524080851/http://www.ihealthrecord.org/forPhysicians.html, [retrieved from the internet on Nov. 7, 2013], 2 pages.

iHEALTHRECORD FAQs, https://web.archive.org/web/20050525032329/http://www.ihealthrecord.org/faq.html, [retrieved from the internet on Nov. 7, 2013], 15 pages.

Medicarecord.com, https://webarchive.org/web/19991012053847/http://medicalrecord.com/, [retrieved from the internet on Nov. 5, 2013], 2 pages.

Medicalrecord.com, https://web.archive.org/web/19991012063749/http://medicalrecord.com/press.asp, [retrieved from the internet on Nov. 4, 2013], 5 pages.

Help Center, https://web.archive.org/web/20040404033910/http://personalmd.com/help/efile.shtml, [retrieved from the internet on Nov. 7, 2013], 2 pages.

Synchart, https://web.archive.org/web/20040614051913/http://www.synchart.com/pages/system.html, [retrieved from the internet on Nov. 7, 2013], 3 pages.

Synchart, https://web.archive.org/web/20040614063122/http://www.synchart.com/pages/system.html, [retrieved from the internet on Nov. 7, 2013], 5 pages.

Walgreens, https://web.archive.org/web/20010815043713/http://www.walgreens.com/, [retrieved from the internet on Nov. 5, 2013], 1 page.

(56) References Cited

OTHER PUBLICATIONS

Walgreens, https://web.archive.org/web/20010801143713/http://www.walgreens.com, [retrieved from the internet on Nov. 5, 2013], 1 page.

Walgreens Pharmacy, Mar. 3, 2000, http://web.archive.org/web/20000303091027/http://www.walgreens.com/pharmacy/default [retrieved from the internet Jun. 24, 2013] 1 page.

Walgreens Historical Highlights, http://www.walgreens.com/marketing/about/press/facts/fact3.jsp [retreived from internet Aug. 13, 2013], 6 pages.

National Committee on Vital and Health Statistics, Letter to Honorable Michael O. Leavitt, Secretary, U.S. Department of Health and Human Services dated Sep. 9, 2005, 11 pages. http://ncvhs.hhs.gov/050909It.htm.

U.S. Department of Health and Human Services, "A Report Recommendation From the National Committee on Vital and Health Statistics, Personal Health Records and Personal Health Record Systems", Feb. 2006, 35 pages.

Szolovits, Peter, et al., "Guardian Angel: Patient-Centered Health Information Systems", Massachusetts Institue of Technology dated May 1994, 43 pages, http://groups.csail.mit.edu/medg/projects/ga/manifesto/GAtr.html.

* cited by examiner

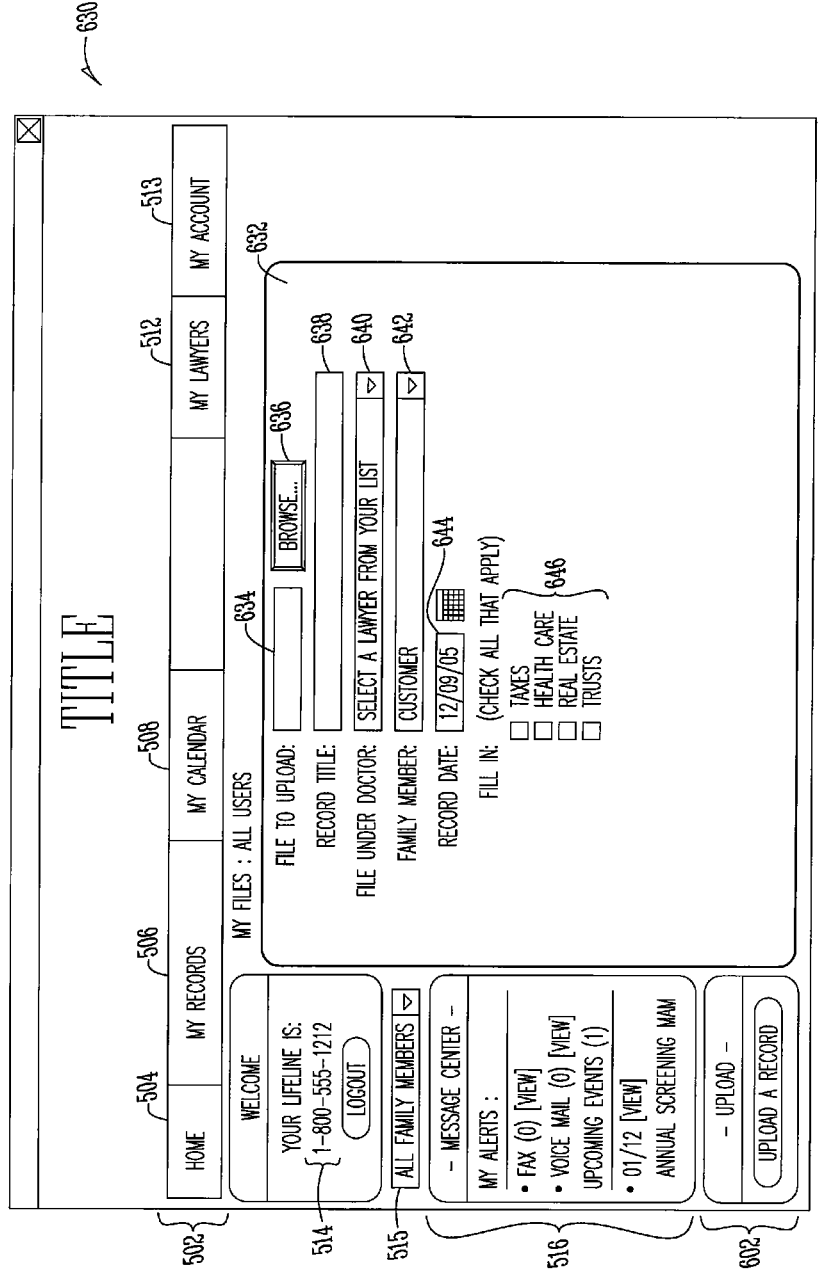

METHOD AND SYSTEM FOR PROVIDING ONLINE RECORDS

PRIORITY STATEMENT

This application is a continuation-in-part of, and claims priority to, U.S. patent application Ser. No. 11/225,518, filed Sep. 12, 2005, hereby incorporated by reference in its entirety.

BACKGROUND OF THE INVENTION

The present invention relates to the provision of online records, including financial and legal documents and managing of financial and legal services. More particularly, the present invention relates to providing a means for consumers to request their legal documents from legal service providers, store their legal documents, and provide for private communications between the consumers and their legal service providers.

Legal documents can be particularly sensitive communications. Laws and attorney regulations place confidentiality limitations on legal records. In addition, certain legal documents such as legal opinions communicated from attorneys to clients may be privileged communications. The privilege may be lost if the information is communicated to others.

In addition to legal records, certain records may be closely associated with legal records. These include certain health records such as health care power of attorneys. In addition certain financial records may be associated with legal records, such as those financial records necessary for preparing tax returns or other financial disclosures.

One problem with legal documents is the number of such documents which an individual, family, or small business, will develop over time. If all records are maintained, organization of the documents may be difficult and time-consuming. Without proper organization, finding particular records can be time-consuming or otherwise problematic.

To some extent, service providers may be relied upon to maintain certain records. For example, lawyers or accountants may maintain copies of certain records for a limited time. However, they may charge a fee for providing copies of records. In addition, they may have document retention policies which require destruction of records after a given time period. Thus, individuals or other entities maintain their own copies of legal records, financial records, and other types of records.

Of course, whenever records are routinely maintained by an individual or service providers such as lawyers or accountants, there is still the possibility of records being destroyed such as in fires, earthquakes, hurricanes, and the like. Thus there are various problems with maintaining legal, financial records, and related records.

Another problem relates to conveying legal records. It should be appreciated than individual or entity may be represented by multiple attorneys or law firms for different matters. As such, a great deal of correspondence and documentation may be generated and communicated back and forth between a customer and each attorney. Such information may be difficult to organize as previously discussed. In addition, documents relating to a matter associated with one attorney may be relevant to another matter being handled by another attorney. Thus, it may difficult, time-consuming, costly, or otherwise problematic to selectively disseminate information between attorneys, accountants, or other service providers.

Another problems relates to the offering of unbundled legal services. Recently, there has been increased interest in lawyers providing unbundled legal services to their clients. In such instances, a client takes on more responsibility and the lawyer takes on less responsibility with limited representation. Unbundled legal services provides the potential advantage to the client of being able to reduce legal costs. Yet, lawyers may be resistant to providing unbundled legal services because significant time and effort may be required to limit their representation and determine whether unbundled legal services are appropriate in a particular instance. In addition, collection of information from clients or potential clients can be problematic, and multiple requests for information or other documentation from clients or potential clients may be required. Moreover, because of the reduced reliance on lawyers to provide legal services, it is increasingly important that an individual or entity maintain their own complete legal records.

Another problem relates to the use of prepaid legal services. Prepaid legal services typically involve an individual or group employee benefit plan in which members pay a periodic charge (such as a monthly fee or premium) in exchange for access to certain legal services. In such instances, it becomes increasingly important for individual members to be able to be able to provide documentation to the lawyer or lawyers who provide services under the plans and for the lawyer or lawyers to be able to communicate with the individual members in a cost effective manner. There may be significant lawyer time or administrative overhead in communicating necessary legal documents and other information back and forth between an attorney and a client.

Thus, there is a general lack of recognition of the need to provide secure and private communications between a legal or financial services provider and their client and to do so in a manner that is convenient for both the provider and the client. There is also a general lack of recognition of the problems for an individual to be able to store and maintain those records in one secured, password protected account that allows for files to be organized.

BRIEF SUMMARY OF THE INVENTION

Therefore it is a primary object, feature, or advantage of the present invention to improve upon the state of the art.

It is a further object, feature, or advantage of the present invention to facilitate privacy of legal records.

A still further object, feature, or advantage of the present invention is to provide an individual with meaningful access to their legal records.

Yet another object, feature, or advantage of the present invention is to provide for placing an individual in control of their legal records and allowing them to selectively provide access to others.

A still further object, feature, or advantage of the present invention is to provide a method to store, organize, and annotate legal records and also to customize the storage by giving the user the ability to name the folders in which those records are stored.

Another object, feature, or advantage of the present invention is to give users the ability to upload images.

Yet another object, feature, or advantage of the present invention is to give users the ability to forward records via fax to a healthcare provider.

A further object, feature, or advantage of the present invention is to provide a means for individuals to store and access not only legal documents, but other types of related information, including health care records.

One or more of these and/or other objects, features, or advantages of the present invention will become apparent from the specification and claims that follow.

According to one aspect of the present invention, a method for providing a user with the ability to access and collect legal records associated with the user is provided. The method includes assigning a phone number to the user for fax and voice communications from a legal services provider and associating access information with the user for the user to use to access a secure web site. The method further includes providing the user with a document to provide to the legal services provider exercising rights of the user for access to the legal records, the document requesting the legal services provider to send the legal records to the phone number. The method further includes receiving a private fax communication comprising a legal record associated with the consumer for which the consumer has requested and given permission to the legal services provider to send, converting the private fax communications into an image file format, and storing the legal services record encoded in the image file format. The method further includes providing the user with secure access to the web site using the access information and providing on the web site an interface to the legal records of the user for the user to access the legal record.

According to another aspect of the present invention, a method for providing a user with the ability to access and collect legal records associated with the user through use of a user account is provided. The method includes assigning a destination address individually associated with the user account for receiving communications from at least one legal service providers and associating access information with the user account for the user to use to access a secure web site. The method further includes receiving a communication from one of the at least one legal services providers, the communication directed to the destination address, the communication comprising a legal record associated with the user for which the user has requested and given permission to the legal services provider to send. The method further includes storing a representation of the legal record and providing the user with secure access to the web site using the access information and providing on the web site an interface to the legal records of the user for the user to use.

According to another aspect of the present invention, a method for providing a user with the ability to access, collect, and share legal records associated with the user through use of a user account is provided. The method includes assigning a destination address individually associated with the user account for receiving communications from at least one legal service providers, associating access information with the user account for the user to use to access a secure web site, and receiving a communication from one of the at least one legal services providers, the communication directed to the destination address, the communication including a legal record associated with the user for which the user has requested and given permission to the legal services provider to send. The method further includes storing a representation of the legal record, providing the user with secure access to the web site using the access information; and providing on the web site an interface to the legal records of the user for the user to use to view, organize the legal records and send the legal records to one or more additional legal services providers.

According to another aspect of the present invention, a method for providing a user with the ability to access, collect, and share legal records associated with the user through use of a user account is provided. The method includes assigning an identifier associated with the user account for receiving communications from a plurality of legal service providers, associating access information with the user account for the user to use to access a secure web site, and receiving legal communications from the plurality of legal service providers. The legal communications are directed to the user account using the identifier and each of the legal communications include information associated with the user for which the user has requested and given permission to the legal services providers to send. The method further includes storing a representation of the legal communications, providing the user with secure access to the web site using the access information, and providing on the web site an interface to the legal communications of the user for the user to use to view, organize the legal communications and send copies of the legal communications to one or more of the plurality of legal services providers.

BRIEF DESCRIPTION OF THE DRAWINGS

FIG. 11 is a screen display for an uploaded file feature according to another embodiment of the present invention.

DETAILED DESCRIPTION OF THE PREFERRED EMBODIMENT

The present invention provides for a convenient method for individuals to collect and store their private information, including legal, financial, insurance, medical, and related information and to provide private communications between the individual and their service providers who generate the information or documents or need to access the information or documents. One of the ways that the present invention collects and stores private medical information and facilitates private communications is through use of secure fax and voice communications. One method for providing secure fax and voice communications is to provide a dedicated toll-free number for fax and voice communications. This dedicated toll-free number provides direct and private communications between a service provider and their customer so that a service provider can be assured that they are maintaining customer communications in secret and to avoid violating applicable privacy laws or customer expectations regarding privacy.

Figure 1:
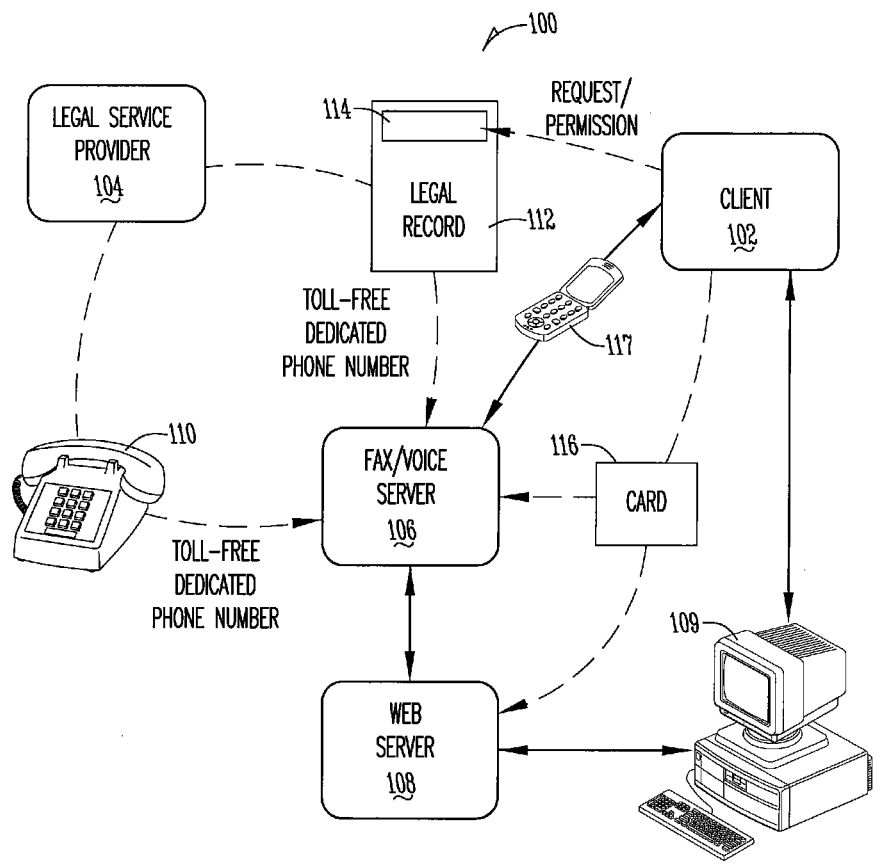
FIG. 1 is diagram illustrating one embodiment of a system of the present invention.

FIG. 1 is a diagram illustrating one embodiment of a system 100 of the present invention. In FIG. 1, a consumer 102 is shown. A legal service provider 104 is also shown as well as a fax/voice server 106. A web server 108 is operatively connected to the fax/voice server 106. The legal service provider 104 uses the phone 110 to communicate private voicemail messages through a toll-free dedicated phone number to the fax/voice server 106. In addition, the legal service provider faxes legal records 112 to the fax/voice server 106 using the toll-free dedicated phone number. As used herein, the term "legal records" refers to legal documents or documentation or other legal communications. The legal records 112 or a folder for containing the legal records preferably has a sticker 114 present. The sticker 114 indicates or instructs the service provider 104 or their staff to fax the information to the toll-free dedicated phone number. In addition, the sticker 114 provides an indication of clear consent from the consumer 102 to the legal services provider 104 to the toll-free dedicated phone number. Thus, it becomes a simple process for a consumer 102 to provide their legal services provider 104 with instructions to fax legal records, a simple process for the legal services provider 104 to obtain permission to fulfill a request for legal services, and a simple process for the legal services provider 104 to do so in a secure and convenient manner as the fax is going directly to a toll-free dedicated phone number associated with the customer 102.

The web server 108 is operatively connected to the fax/voice server 106 such as over a network or otherwise. A customer 102 or their proxy can communicate directly with the web server 108 through a computing device 109 or the fax/voice server 106 using a phone 117. The patient 102 can use a card 116 that contains access information to log on to the web server 108 associated with a web site of the present invention, or as a reminder of their toll free dedicated phone number which they can call to access voicemail messages, listen to text-to-speech conversion of emails, or otherwise access information.

The present invention also allows a user 102 to upload files using a computing device 109 to the web server 108. In addition, the user 102 can use the computing device 109 to interact with the web server 108 to specify that a legal record or records needed to prepare a legal document is faxed via the fax/voice server 106 to a legal services provider 104.

Figure 2:
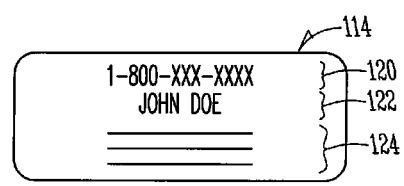
FIG. 2 is a pictorial representation of a sticker authorizing transmissions of records to the user account according to one embodiment of the present invention.

FIG. 2 illustrates one embodiment of a sticker 114 for a user to give to their legal service provider to request or instruct their legal service provider to fax communications to the toll free dedicated phone number associated with the consumer. Although it is preferred that a sticker 114 be used because of the added convenience provided by being able to permanently or semi-permanently attach to a file at the legal service provider's office, the present invention contemplates that other types of documents could be used. The sticker 114 includes the phone number 120 which is preferably a toll free dedicated phone number associated with the patient. Note that there is no pin number required which greatly simplifies the process of faxing documents. In addition, the name 122 of the consumer is shown. There is also a written request 124 on the sticker 114 that instructs the legal services provider to fax the records and explicitly gives permission to fax the communications. The language of the written request 124 may vary as necessary to comply with any applicable laws or regulations. It should be appreciated that the sticker 114 provides great convenience to both an individual who wants to instruct their legal services provider to give them access to their legal records as well as to the legal services provider who can now easily provide the individual with access to their legal service records.

Figure 3:
FIG. 3 illustrate a card with legal record access information according to one embodiment of the present invention.

FIG. 3 illustrates one embodiment of a wallet card 116. The wallet card has a front side 130 and an opposite back side 132. The card 116 includes the name of the individual 122, a URL for a web site 136 which stores legal records for the individual. In addition there is access information 134 such a username and password. The card 116 also includes the toll free dedicated phone number 120 associated with the individual. Additional information may be placed on the back side 132 of the card 116.

The present invention contemplates including the sticker 114 (or other permission/request document) and the card 116 in a welcome kit when an individual or family subscribes or signs-up for the service. In addition, from the web site associated with the service, preferably addition stickers and/or additional cards can be printed and information can be updated as necessary.

Figure 4:
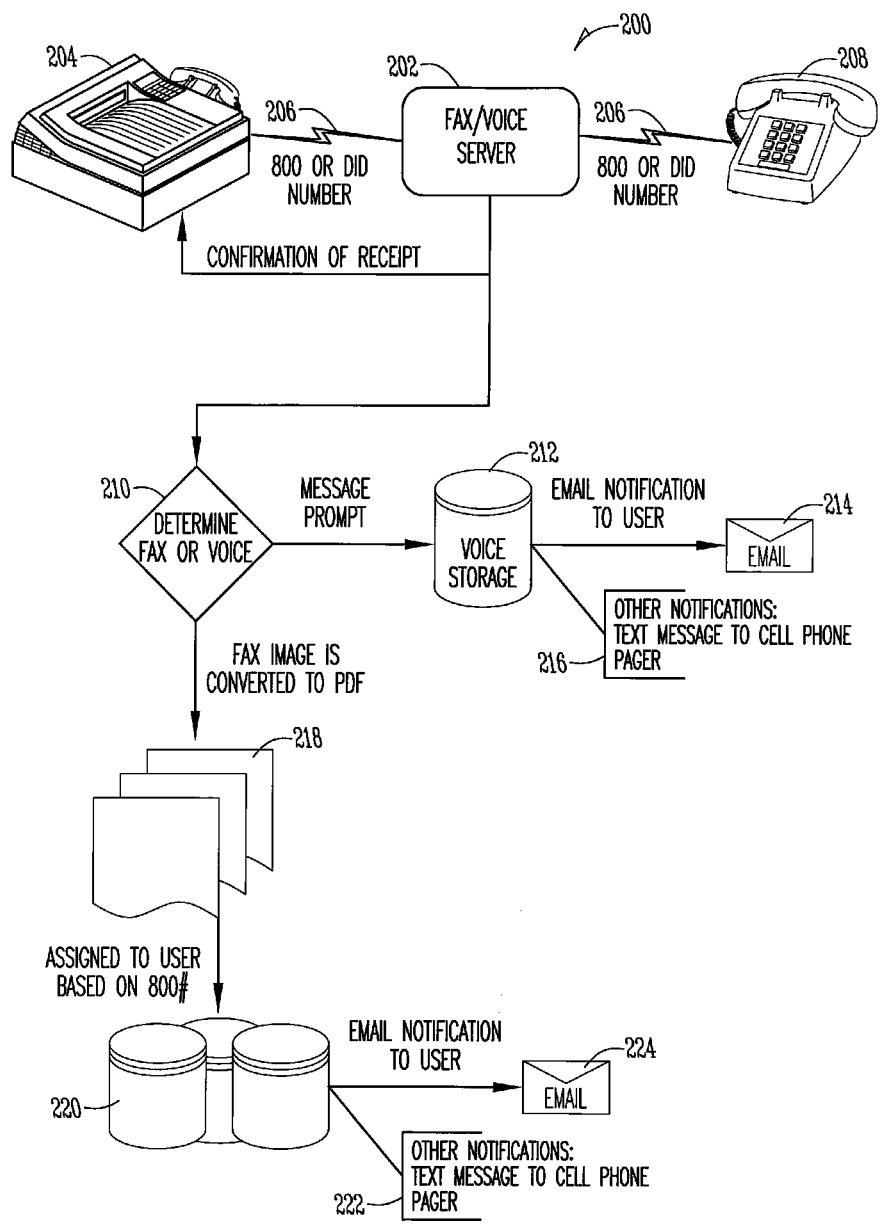
FIG. 4 is a diagram illustrating one embodiment of a system of the present invention.

FIG. 4 illustrates one embodiment of a system of the present invention. Preferably such a system is implemented using equipment from Prairie Systems, Inc. of Omaha, Nebr., although the present invention contemplates that other vendors may be used. As shown in FIG. 4, the system 200 includes a fax/voice server 202. The fax/voice server 202 is accessible by a fax machine 204 or a phone 208 through using a dedicated phone number 206. Preferably, the phone number 206 is toll-free as this increases the accessibility and convenience of the system which is very important. However, the phone number 206 could also be a direct dial phone number. When the fax/voice server 202 receives a call, a determination is made in step 210 as to whether the call is a voice call or a fax call. Where the call is a voice call, an interactive voice response (IVR) system is used to determine who the caller is, the purpose of the call, or other information, and then stores any voicemail message in voice storage 212. The system is adapted to notify the individual that there is a voicemail message through an email notification in step 214 and/or other types of notification in step 216. Other types of notification can include, but are not limited to text messages to a cell phone or pager. Thus, a legal services provider can call the number 206 and leave a voicemail message for the individual and know that the communication is a private communication. Thus, the legal services provider can leave private and confidential information, such as the results of a court decision or administrative action, or the need to schedule a new appointment, or other information. The individual is alerted to the presence of the voicemail message and can then call-in to the fax/voice server 202 to check messages.

Where documents are faxed, fax images are collected and converted to portable document format (PDF) documents 218. Although, the PDF format is preferred, the present invention contemplates that other types of document conversions can be done as may be appropriate in a particular implementation of the present invention. Based on the dedicated phone number 206 used to send the documents, the faxed documents are assigned to a user account and stored in step 220. The individual is alerted via email that the documents have been sent in step 224. Alternatively, the individual is alerted via text messaging in step 222 that a fax has been sent.

Figure 5A:
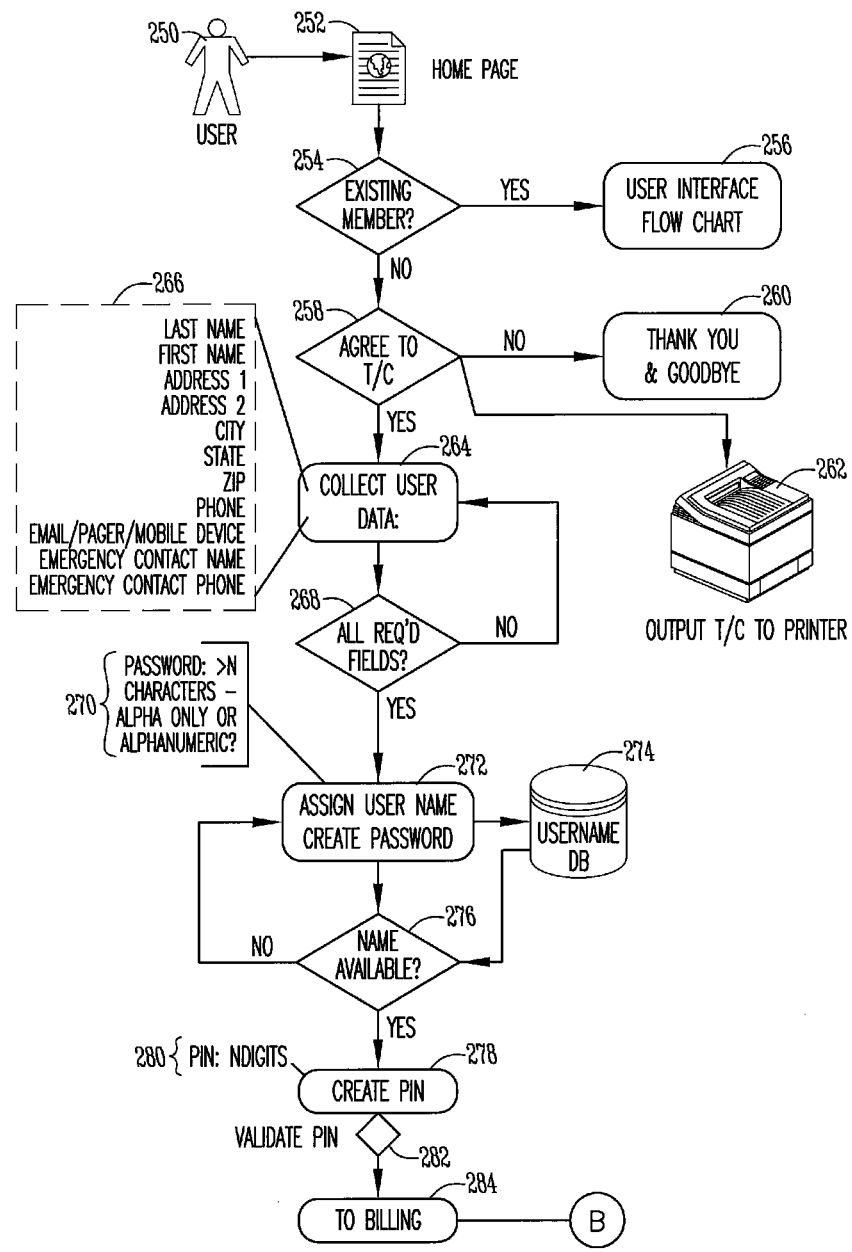
FIG. 5A and FIG. 5B are flow diagrams illustrating an enrollment process according to one embodiment of the present invention.
Figure 5B:
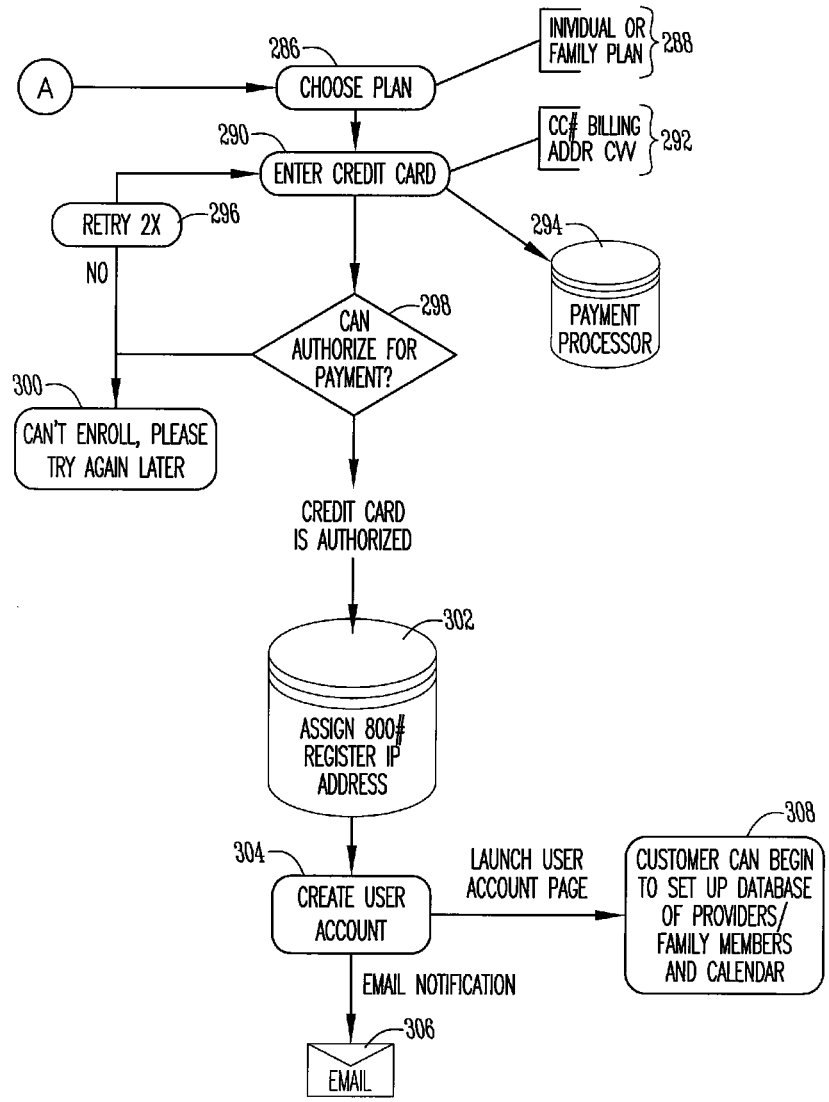
Figure 6:
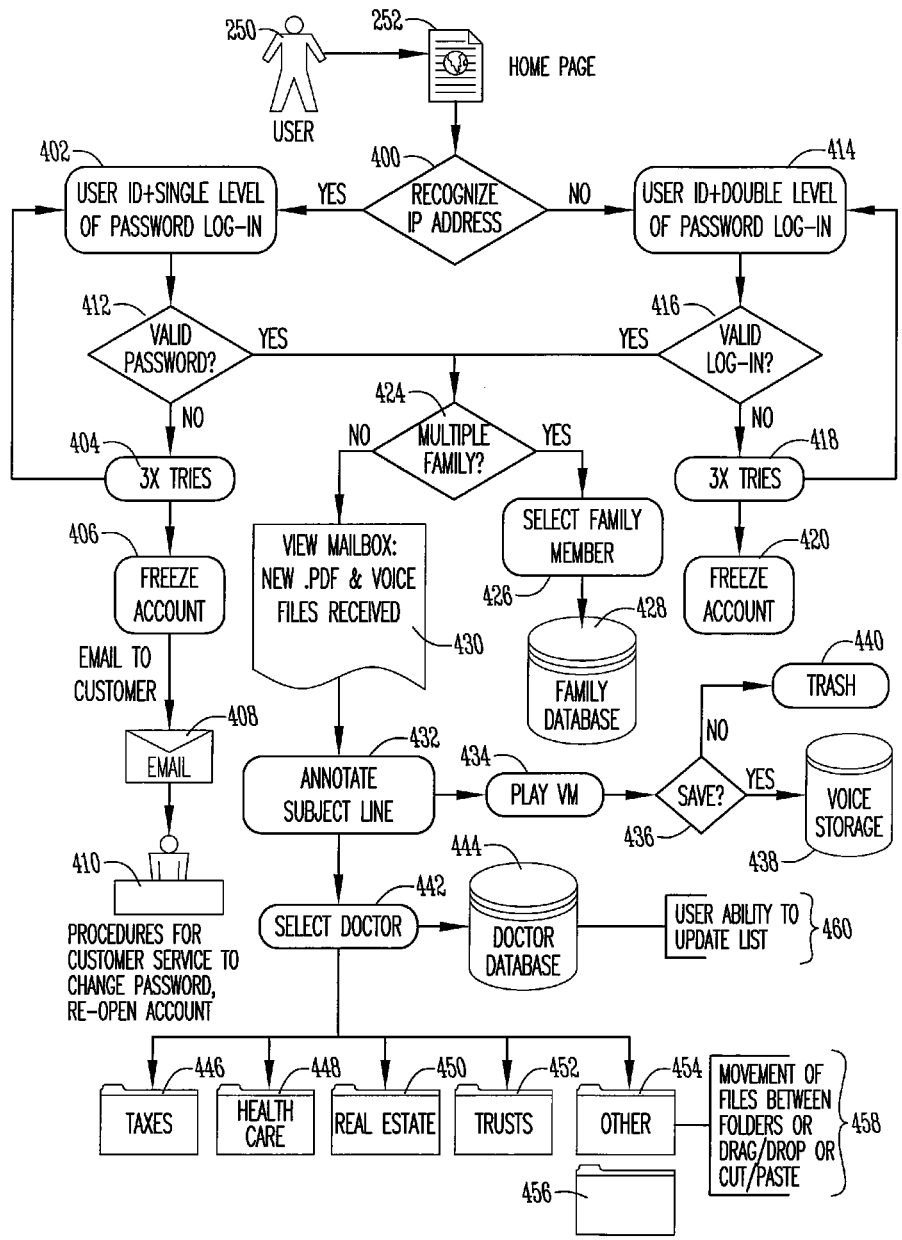
FIG. 6 is a flow diagram for accessing records according to one embodiment of the present invention.

The web site of the present invention provides a convenient location to collect and store healthcare records and provide secure access to the records. It also provides a convenient way to enroll in a service for providing online access to records including legal records. FIGS. 5A and 5B provides one embodiment of an enrollment process In FIG. 5A, a user 250 accesses a home page 252 for a legal records web site. In step 254, a determination is made as to whether the user 250 is an existing member. If the member is, then in step 256 the user is provided access to their user interface as shown in FIG. 6. If not, then in step 258 a determination is made as to whether the user 250 agrees to terms and conditions of service. If not, then in step 260 the user is thanked for their interest but not allowed to continue. The user is also given the option or encouraged to output the terms and conditions to a printer in step 262 so that they can review them closely and maintain a copy for their records if they wish. If in step 258, the user agrees to the terms and conditions of service then in step 264 the system collects user data. User data 266 can include last name, first name, address information, city, state, zip code, phone number, email/pager/mobile device information, emergency contact name, emergency contact phone number, primary care physician phone number, insurance information, allergies and medications, and/or other information. If all fields are received in step 268, then in step 272 the system assigns a user name and password. It is to be understood that the user may also request a particular username and/or set their own password. Where a user selects their own password, then in step 270, a determination is made as to whether the password meets security requirements. For example, there may be a minimum number of characters required, or there must be at least one numeric character, or other requirements. Where the user is allowed to select their own name, in step 274, a username database is searched and in step 276 a determination is made as to whether or not the name is available. If it is, then in 278 the user is permitted to create a personal identification number (PIN). In step 280, a rule such as one requiring a particular number of digits or a particular minimum digits is applied. In step 282 the PIN is validated and the enrollment process proceeds to billing options in step 284. In FIG. 5B, the user is allowed to choose a plan in step 286. The individual could, for example, choose an individual or family plan from the plan options 288. In step 290, the user enters credit card information 292 which may include a credit card number, billing address, and CW number. This information is then submitted to a payment processor 294. In step 298, a determination is made as to whether the credit card information can be authorized for payment. If not, then the number of retries is determined in step 296 and the user is allowed to re-enter their credit card information in step 290. If there have already been two tries to validate credit card information, then in step 300 the individual is told that they can not enroll at this time and should try again later. If payment is authorized in step 298 then in step 302 a dedicated toll free phone number is assigned and an IP address associated with the user is registered. In step 304 a user account is created. In step 306 an email notification confirming registration is sent to the user. In step 308 the user can begin to setup their personal web site such as their database of legal service providers, family members, calendar, and otherwise configure their web site.

Where a calendar is used, the present invention contemplates that the calendar can be synchronized with an application such as Microsoft Outlook, a calendar program associated with a PDA, or other personal information manager.

After registration, the user can access the user interface of the web site. FIG. 6 illustrates one embodiment of the user interface 256. The user 250 can access the homepage 252. In step 400, a determination is made as to whether the system recognizes the ip address being used by the user as being associated with the user. If the ip address is not recognized then extra security measures are taken beginning in step 414. In step 414 a username and a double level of password log-in is required. If a valid log-in, then the process proceeds to step 424. If not, then in step 418, the number of invalid log-in attempts or tries is monitored and if it is three, then in step 420 the account is frozen. Returning to step 400, if the ip address is recognized as being associated with the user, then in step 402 a username and a single level of password log-in is required. In step 412 a determination is made as to whether or not the password is valid. If a valid password, then the process proceeds to step 424. If not, then in step 404 a determination is made as to the number of invalid attempts. After three invalid attempts, in step 406 the account is frozen and in step 408 an email is sent to the individual who may, in step 410, implement procedures to change the password and re-open the account.

Returning to step 424, a determination is made as to whether the account is associated with an individual or a family. If the account is associated with a family, then in step 426, the user can select the family member and access the family database 428. If, in step 424 the account is not a family account, then in step 430 the user can view their mailbox showing new PDF files and voice files. Preferably, these new files include date and time stamps so that the user can see when the files were received.

In step 432, the user is allowed to annotate the messages to better identify the messages in a manner that is convenient for the user. In step 434, the user can play the voicemail messages. In step 436, the user can choose to save the messages to voice storage 438 or to send the message to the trash 440. In step 442, the user can select a legal services provider to associate with the voicemail messages. For example, the lawyer from which the voicemail or imaged document was received. Preferably the lawyer is within the database 444. If not, then in step 460, the user can update the database 444 to include the lawyer. The user can then organize the voicemail or document according to the user's preference into one or more file folders. Examples of file folders may include TAXES 446, HEALTH CARE 448, REAL ESTATE 450, TRUSTS 452, OTHER 454. Any number of types of documents may be included, including financial records, and vital records which may include wills, living wills, healthcare power of attorneys, and related information. The user can make new file folders such as file folder 456 and identify it appropriately. The user interface offers functions 458 such as movement of files between folders, drag and drop, cut and paste, and/or other functions that will assist the user in organizing their records.

The present invention provides for each of the file folders to be protected with one or more additional passwords. Such an implementation is particularly useful in a number of contexts. For example, the use of multiple passwords allows information such as insurance information, financial information, or other proprietary information, medical records, and other type of information to be protected with differing levels of access.

Another example of where this extra layer of security can be useful is where a single account is shared by a family consisting of two parents and multiple children. Each parent may have their own folder separately password protected so that the other parent can not access their folder, but still allowing both parents to access the folders for the children.

Figure 7:
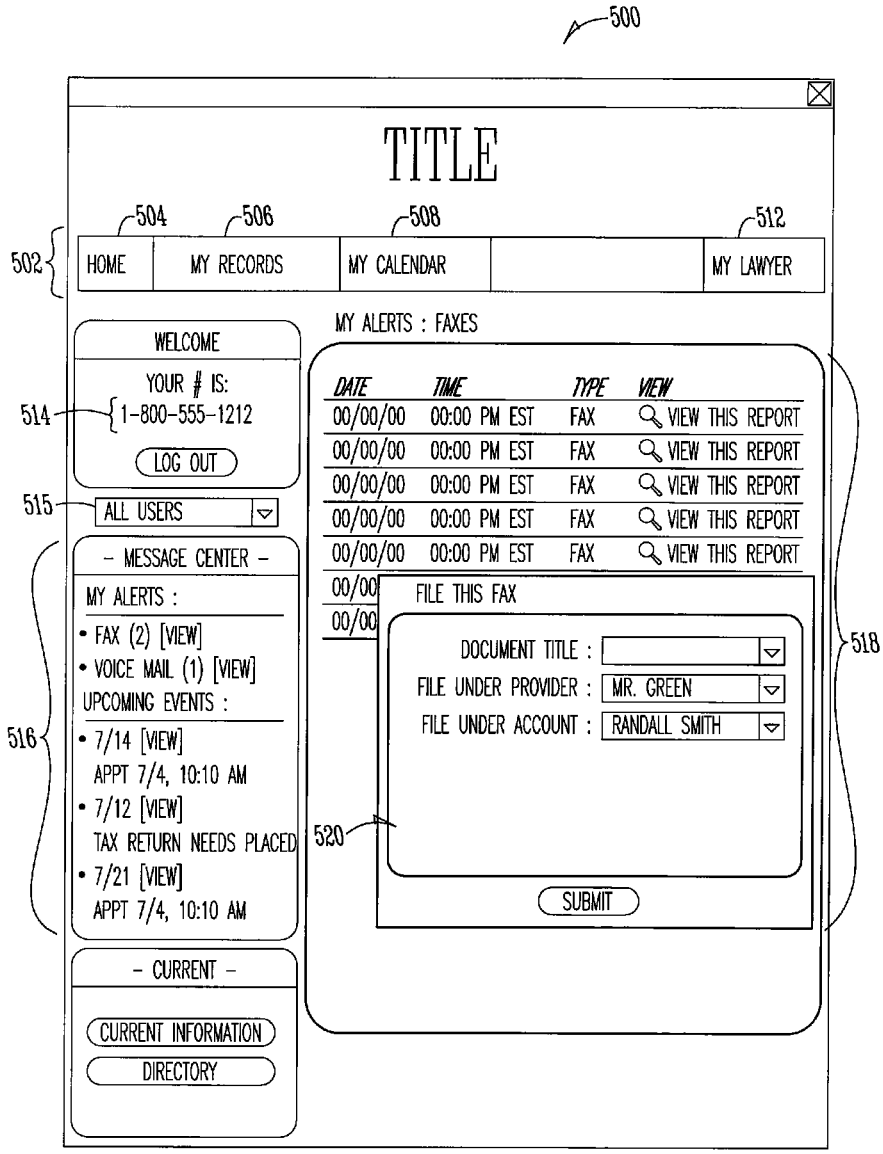
FIG. 7 is a screen display of a web site according to one embodiment of the present invention.

FIG. 7 illustrates one embodiment of a screen display of the present invention. In FIG. 7, the screen display 500 includes a menu bar 502 along the top with different menu items such as "Home" 504, "My Records" 506, "My Calendar" 508, and "My Lawyer" 512. The screen display 500 also includes a reminder to the individual of their toll free dedicated phone number 514. A message center 516 includes alerts as to recent faxes, voicemails, appointments, legal-related deadlines, or other related events. The user can view the recent faxes 518, and for each fax, can file it using fax filing options 520 which allow the user to give a document title to the fax, associate a legal services provider with the fax, file the fax under a particular account where the account is a family account, and identify the fax by type of document.

It should also be appreciated that a user need not fax themselves documents. Instead, the user can upload scanned documents or other files in any number of formats.

Figure 8:
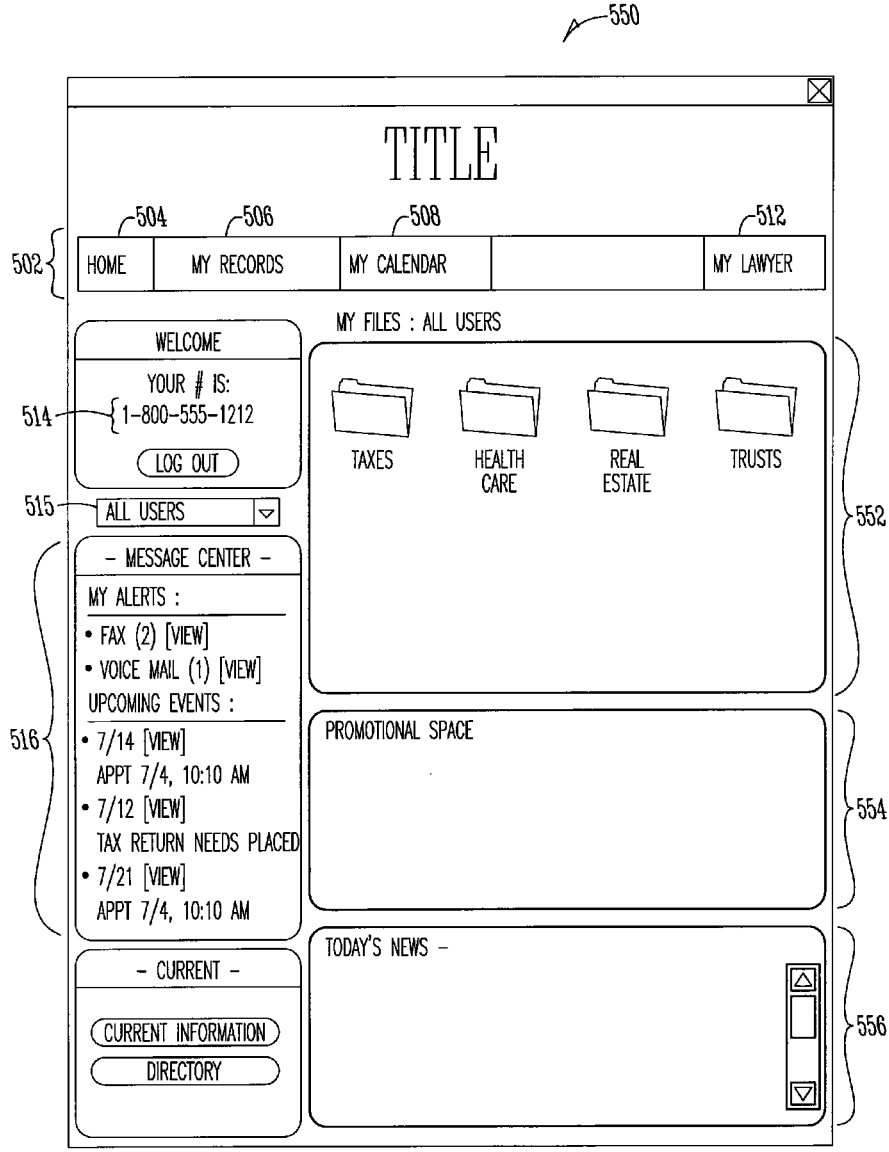
FIG. 8 is another screen display of a web site according to one embodiment of the present invention.

FIG. 8 illustrates another example of a screen display according to one embodiment of the present invention. In FIG. 8, the screen display 550 also includes a files section 552 wherein different folders are shown for storing and organizing information. This allows a user to store records in a manner appropriate for them. In one embodiment, the folders can include separate folders for taxes, health care, real estate, trusts, and other types of records. As shown in FIG. 8, there is a promotional space 554. The present invention allows for promotional material to be placed in the promotional space 554 that is of potential interest to the user. The promotional information can come from a third party source or advertiser. In additions, news information may be placed in a news information portion 556 of the web page. The news information can include breaking news of potential interest or importance to the user.

Figure 9:
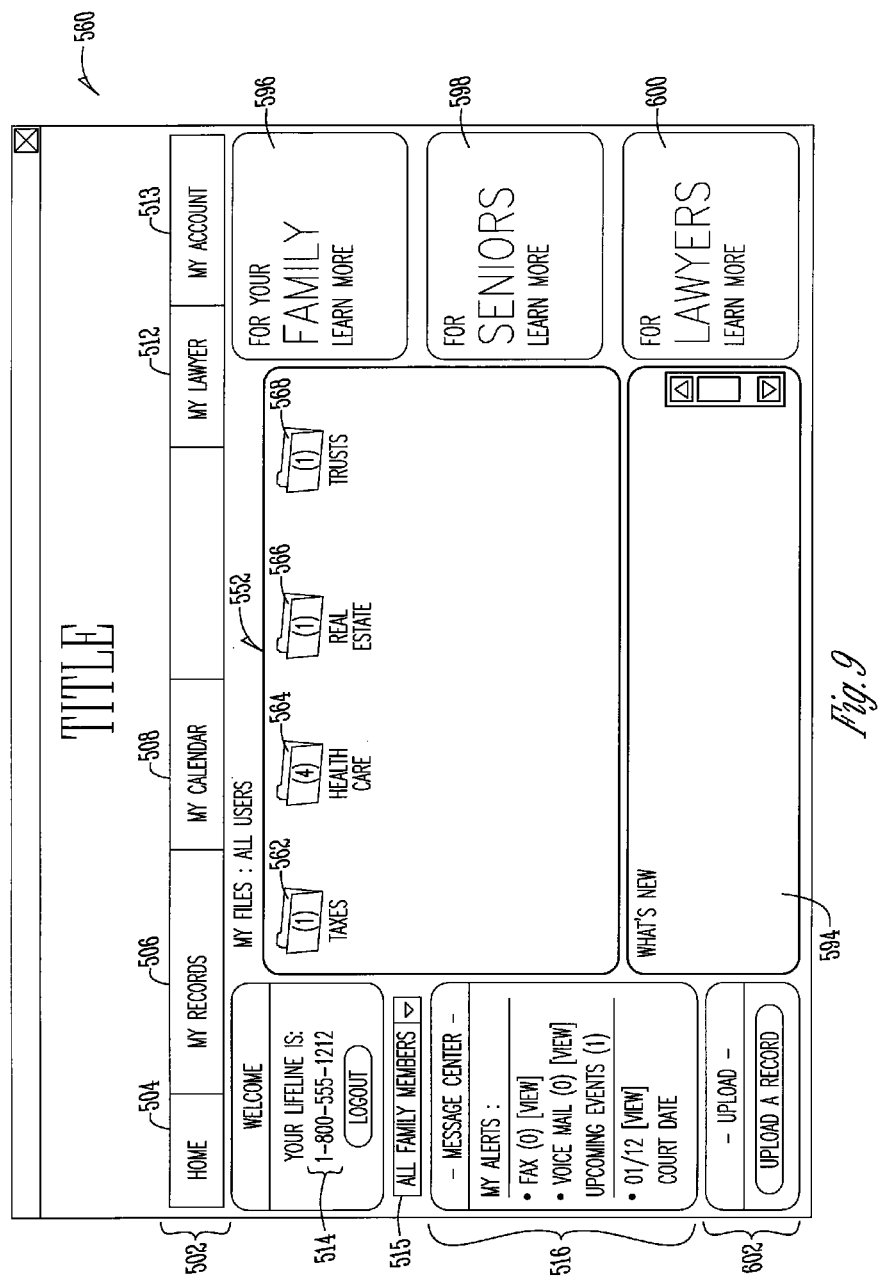
FIG. 9 is a screen display according to one embodiment.

FIG. 9 is another example of a screen display 560 according to one embodiment of the present invention. Note that a MYACCOUNT option 513 is shown near the top of the screen display 560. Also note that a user is allowed to select a family member using the dropdown list box 515. There is also an upload record option 602 provided so that a user may upload files of various types directly to their account.

Shown in the MY FILES portion 552 are a plurality of file folders, including: TAXES folder 562, HEALTH CARE folder 564, REAL ESTATE folder 566, TRUSTS folder 568. The various file folders shown provide a convenient method for users to organize their files. Of course any number of additional file folders may be added. Note that each folder indicates how many files are stored within the file folder.

A WHAT'S NEW portion 594 allows users to learn about new features or other information. A FAMILY panel 596 can display information or links to information relevant to families. A SENIORS panel 598 can display information or links to information relevant to seniors. A LAWYERS panel 600 can display information or link to information relevant to lawyers. Of course, the present invention contemplates that panels 596, 598 and 600 need not be present, and where present can be used to convey other types of information of potential interest to users.

Figure 10:
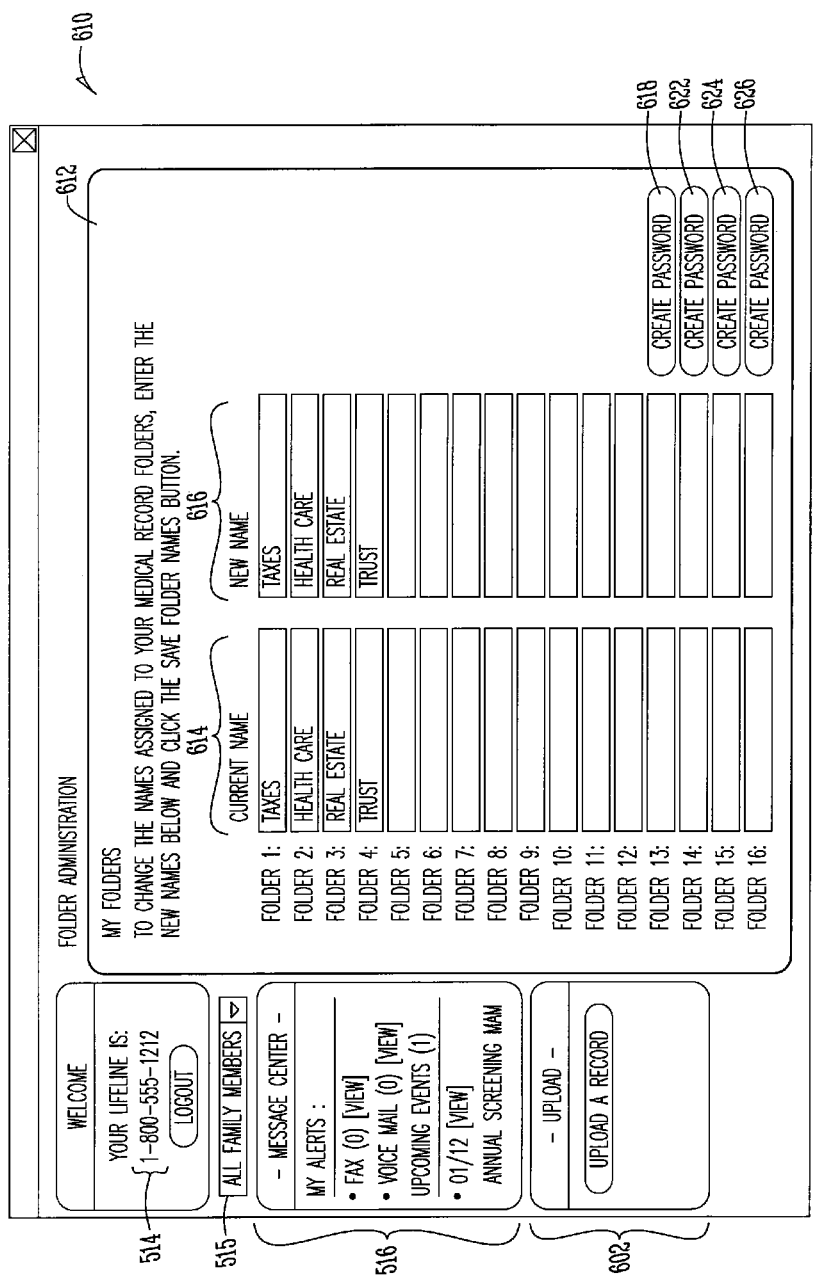
FIG. 10 is a screen display for folder administration according to another embodiment.

FIG. 10 is another example of a screen display according to one embodiment of the present invention. The screen display 610 allows for folder administration. A folder administration portion 612 includes a listing of multiple folders (16 shown) with a column 614 indicating the current name for each folder and a column 616 indicating the new name to be assigned to each folder. In operation a user can change the name of the folders to suit their particular needs. Note that at least a portion of the folders have a password associated with them. This allows a to create a password such as by pressing buttons 618, 622, 624, 626, This provides an additional layer of security to these files.

FIG. 11 is a screen display for an uploaded file feature according to another embodiment of the present invention. The screen display 630 allows for uploading a legal record 602. The upload a record window 632 allows the user to select a file to be uploaded 634 by browsing 636 to the location of the stored file. For example, if the user has an image saved in a picture format such as a jpeg, they would be able to browse 636 to the file and upload the file 634 to add to or to make current their present set of records. The upload a record window 632 also allows the user to record a title 638 for the file uploaded 634. Additionally, the uploaded a record window 632 allows the user to associate the file uploaded 634 with the appropriate lawyer selected from a drop-down list 640. If the account is family or joint type account and allows storing legal records for multiple persons, the user may use the dropdown menu 642 to select the family member 642 to whom this newly uploaded file 634 should be associated with. The upload a record window 632 also allows the user to record a date 644 associated with the newly uploaded file 634. Lastly, the user has the option of selecting the individual folders 646 where he or she would like a copy of the newly uploaded file 634 to be saved. For example, the user may wish to save the same document in multiple folders. The upload a record window 632 allows the user to periodically update their records with important medical information and associate that information with the appropriate folders. The upload a record window 632 also makes it easy for the user to browse to and save legal files in electronic form in a convenient and organized manner.

In one embodiment, not only is a password required to access the website, but an additional password is required to access such a folder. This feature can be advantageous in a number of different situations. For example, a family may share an account, but each spouse may maintain certain files in confidence from the other. As shown there are buttons 618, 622, 624, 626 for providing a secondary level of password protection.

The present invention contemplates numerous options, variations, and alternatives. For example, legal service providers may be legal service providers made available through prepaid legal services, including those made available through an employer sponsored plan. In addition, the legal service providers may provide either bundled or unbundled legal services.

The present invention is not to be limited to the specific disclosure provide herein. The present invention contemplates numerous variations as may be appropriate in a particular context, environment, or situation.

What is claimed is:

1. A method for providing a user with the ability to access and collect legal records associated with the user, comprising:
assigning a phone number to the user through a secure web site for fax and voice communications from a legal services provider;
associating access information with the user for the user to use to access the secure web site on a server;
providing the user with a document to provide to the legal services provider exercising rights of the user for access to the legal records, the document requesting the legal services provider to send the legal records to the phone number;
receiving a private fax communication at a fax server, the private fax communication comprising a legal record associated with the consumer for which the consumer has requested and given permission to the legal services provider to send;
converting the private fax communications into an image file format at the fax server;
storing the legal services record encoded in the image file format on the server;
providing the user with secure access to the web site on the server using the access information and providing on the web site an interface to the legal records of the user for the user to access the legal record;
receiving voice communications message from the legal services provider to the user and maintaining the voice communications message as private;
alerting the user of the voice communications message from the legal services provider and providing the user with access information to access the voice communications message through the web site; and creating a wallet card from the web site by providing the user with functionality to update information on the wallet card and print the wallet card, wherein the information included on the wallet card comprises access information and the destination address.

2. The method of claim 1 wherein the document is a sticker adapted for attachment to the legal record a file associated with the user.

3. The method of claim 1 wherein the web site interface further provides for organizing and annotating the legal records by the user into separate file folders with functionality for the user to name the file folders and add file folders.

4. The method of claim 1 further comprising alerting the user of a fax transmission from the legal services provider.

5. The method of claim 4 wherein the alerting comprises sending a text message to the user.

6. The method of claim 4 wherein the alerting comprises sending an email to the user.

7. The method of claim 4 wherein the alerting comprises sending a voice message to the user.

8. The method of claim 1 further comprising providing on the web site means to calendar an appointment with a legal services provider.

9. The method of claim 8 further comprising sending a reminder regarding the appointment with the legal services provider.

10. The method of claim 9 wherein the reminder is a text message.

11. The method of claim 9 wherein the reminder is an email.

12. The method of claim 9 wherein the reminder is a voice message.

13. The method of claim 1 further comprising receiving payment from the user for facilitating access to the legal records associated with the user.

14. The method of claim 1 further comprising creating stickers from the web site and requesting legal service providers to fax legal records to the phone number, wherein the stickers include information requesting legal service providers to fax legal records to the phone number.

15. The method of claim 1 further comprising providing means for protecting documents with at least one additional layer of password protection.

16. The method of claim 1 wherein the phone number is individually associated with the user.

17. The method of claim 16 wherein the phone number is a toll-free phone number.

18. A method for providing a user with the ability to access and collect legal records associated with the user through use of a user account, the method comprising:

assigning a destination address through a secure web site, the destination address individually associated with the user account for receiving communications from at least one legal service providers;

associating access information with the user account for the user to use to access the secure web site;

receiving a communication from one of the at least one legal services providers at the web site, the communication directed to the destination address, the communication comprising a first legal record associated with the user for which the user has requested and given permission to the legal services provider to send;

storing a representation of the first legal record at the web site;

providing the user with secure access to the web site using the access information;

receiving a second legal record from the user uploaded to the web site;

providing on the web site an interface to the legal records of the user, including the first legal record and the second legal record, for the user to use;

wherein the interface further provides for organizing and annotating the legal records by the user into separate file folders with functionality for the user to name the file folders and add file folders;

wherein the interface further provides for providing means to assign additional password protection to one or more of the file folders; and creating a wallet card from the web site by providing the user with functionality to update information on the wallet card and print the wallet card, wherein the information included on the wallet card comprises access information, the destination address, and information regarding prepaid legal services, wherein at least one of the legal service providers are associated with prepaid legal services.

19. The method of claim 18 wherein the destination address is a phone number.

20. The method of claim 19 wherein the phone number is a toll-free phone number.

21. The method of claim 18 wherein the destination address is an email address.

22. The method of claim 18 wherein the destination address is embedded in a bar code.

23. The method of claim 18 wherein the access information includes a first set of access information for providing a first level of security and at least one second set of access information for providing an additional level of security.

24. The method claim 18 wherein the legal record comprises a vital document.

25. A method for providing a user with the ability to access, collect, and share legal records associated with the user through use of a user account, the method comprising:

assigning through a secure web site a destination address individually associated with the user account for receiving communications from at least one legal service providers;

associating access information with the user account for the user to use to access the secure web site on a server;

receiving a communication from one of the at least one legal services providers at the server, the communication directed to the destination address, the communication comprising a legal record associated with the user for which the user has requested and given permission to the legal services provider to send;

storing a representation of the legal record at the server;

providing the user with secure access to the web site on the server using the access information;

providing on the web site an interface to the legal records of the user for the user to use to view the legal records, organize the legal records and send the legal records to one or more additional legal services providers; and creating a wallet card from the web site by providing the user with functionality to update information on the wallet card and print the wallet card, wherein the information included on the wallet card comprises access information, the destination address, and information regarding prepaid legal services, wherein at least one of the legal service providers are associated with prepaid legal services.

26. The method of claim 25 wherein the prepaid legal services being provided by an employer sponsored plan.

27. The method of claim 25 wherein at least one of the at least one legal service providers provides unbundled legal services to the user.

28. A method for providing a user with the ability to access, collect, and share legal records associated with the user through use of a user account, the method comprising:

assigning through a secure web site an identifier associated with the user account for receiving communications from a plurality of legal service providers;

associating access information with the user account for the user to use to access the secure web site stored on a server;

receiving legal communications from the plurality of legal service providers at the server, the legal communications directed to the user account using the identifier, each of the legal communications comprising information associated with the user for which the user has requested and given permission to the legal services providers to send;

storing a representation of the legal communications on the server;

providing the user with secure access to the web site using the access information;

providing on the web site an interface to the legal communications of the user for the user to use to view, organize the legal communications and send copies of the legal communications to one or more of the plurality of legal services providers; and creating a wallet card from the web site by providing the user with functionality to update information on the wallet card and print the wallet card, wherein the information included on the wallet card comprises access information, the destination address, and information regarding prepaid legal services, wherein at least one of the legal service providers are associated with prepaid legal services.

* * * * *